(12) United States Patent
Harynuk et al.

(10) Patent No.: US 8,666,677 B2
(45) Date of Patent: Mar. 4, 2014

(54) AUTOMATED, OBJECTIVE AND OPTIMIZED FEATURE SELECTION IN CHEMOMETRIC MODELING (CLUSTER RESOLUTION)

(75) Inventors: James Harynuk, Edmonton (CA); Nikolai Sinkov, Edmonton (CA)

(73) Assignee: The Governors of the University of Alberta, Edmonton, Alberta (CA)

(*) Notice: Subject to any disclaimer, the term of this patent is extended or adjusted under 35 U.S.C. 154(b) by 0 days.

(21) Appl. No.: 13/518,420

(22) PCT Filed: Dec. 15, 2010

(86) PCT No.: PCT/CA2010/001957
§ 371 (c)(1),
(2), (4) Date: Jun. 22, 2012

(87) PCT Pub. No.: WO2011/075818
PCT Pub. Date: Jun. 30, 2011

(65) Prior Publication Data
US 2012/0259609 A1    Oct. 11, 2012

Related U.S. Application Data

(60) Provisional application No. 61/289,459, filed on Dec. 23, 2009, provisional application No. 61/344,523, filed on Aug. 13, 2010.

(51) Int. Cl.
G01N 33/48 (2006.01)
G01N 33/50 (2006.01)
G06F 19/24 (2011.01)
G06F 19/10 (2011.01)

(52) U.S. Cl.
CPC .............. *G06F 19/24* (2013.01); *G06F 19/10* (2013.01)
USPC ........................................... 702/19

(58) Field of Classification Search
CPC .......... G06F 19/10; G06F 19/24; G06F 19/26
See application file for complete search history.

(56) References Cited

U.S. PATENT DOCUMENTS

2010/0198900 A1    8/2010    Gifford

FOREIGN PATENT DOCUMENTS

WO    03/065282 A1    8/2003
WO    2005/019948 A1    3/2005

OTHER PUBLICATIONS

Frigui et al. Proceedings of the eighth ACM SIGKDD international conference on Knowledge discovery and data mining, 2002, pp. 507-512.*
Williams et al. Journal of the Royal Statistical Society, vol. 21, No. 2, 1959, pp. 396-399.*

(Continued)

*Primary Examiner* — Michael Borin
(74) *Attorney, Agent, or Firm* — Brion Raffoul

(57) ABSTRACT

A novel metric, termed cluster resolution, which compares the separation of clusters of data points while simultaneously considering the shapes of the clusters and their relative orientations. This metric, in conjunction with an objective variable ranking metric, allows for the fully-automated determination of the optimal number of variables to be included in a chemometric model of a system. Cluster resolution is based upon considering the minimum distance between (or the extent of overlap of) confidence ellipses constructed around clusters of points representing different classes of objects. This approach can be generally applied to feature selection for a variety of applications and represents a significant step towards the development of fully-automated, objective construction of chemometric models.

12 Claims, 10 Drawing Sheets

(56) References Cited

OTHER PUBLICATIONS

Rajalahti et al. Chemometrics and Intelligent Laboratory Systems 95 (2009) 35-48.*
Wang et al. Proc. SPIE. vol. SPIE-5812, pp. 31-38. 2005.*
Vogel et al., "PFS Clustering Method", IEEE Transactions on Pattern Analysis and Machine Intelligence, vol. PAM-1, No. 3, Jul. 1979, pp. 237-245.
International Searching Authority, PCT/CA2010/001957 International Search Report and Written Opinion.
P. Doble et al., "Classification of premium and regular gasoline by gas chromatography/mass spectrometry, principal component analysis and artificial neural networks", Forensic Sci. Int., vol. 132, issue 1, Mar. 2003, pp. 26-39.
P. Sandercock and E. Du Pasquier, "Chemical fingerprinting of unevaporated automotive gasoline samples", Forensic Sci. Int., vol. 134, No. 1, 2003, pp. 1-10.
P. Sandercock and E. Du Pasquier, "Chemical fingerprinting of gasoline: 2. Comparison of unevaporated and evaporated automotive gasoline samples", Forensic Sci. Int., 2004, vol. 140, No. 1, pp. 43-59.
P. Sandercock and E. Du Pasquier, "Chemical fingerprinting of gasoline: Part 3. Comparison of unevaporated automotive gasoline samples from Australia and New Zealand", Forensic Sci. Int., 2004, vol. 140, No. 1, pp. 71-77.
I. Wilson et al., "HPLC-MS-based methods for the study of metabonomics", J. of Chromatography B, 2004, vol. 817, pp. 67-76.
S. Bruce et al., "Evaluation of a protocol for metabolic profiling studies on human blood plasma by combined ultra-performance liquid chromatography/mass spectrometry: From extraction to data analysis", Analytical Biochemistry, vol. 372, issue 2, pp. 237-249, 2008.
U. Lutz et al., "Metabolic Profiling of Glucuronides in Human Urine by LC-MS/MS and Partial Least-Squares Discriminant Analysis for Classification and Prediction of Gender", Analytical Chemistry, vol. 78 (13), pp. 4564-4571, 2006.
T. Kind et al., "A comprehensive urinary metabolomic approach for identifying kidney cancer", Analytical Biochemistry, vol. 363, No. 2, pp. 185-195, 2007.
J. Vial et al., "Combination of dynamic time warping and multivariate analysis for the comparison of comprehensive two-dimensional gas chromatograms. Application to plant extracts", J. of Chromatography A 2009, vol. 1216, No. 14 pp. 2866-2872.
R. Mohler et al., "Identification and evaluation of cycling yeast metabolites in two-dimensional comprehensive gas chromatography—time-of-flight-mass spectrometry data", J. of Chromatography A, 2008, vol. 1186, No. 1, pp. 401-411.
R. Mohler et al., "Comprehensive analysis of yeast metabolite GCxGC-TOFMS data: combining discovery-mode and deconvolution chemometric software", Analyst 2007, vol. 132, pp. 756-767.
C. Borges, "Concept for Facilitating Analyst-Mediated Interpretation of Qualitative Chromatographic-Mass Sepctral Data: An Alternative to Manual Examination of Extracted Ion Chromatograms", Analytical Chemistry, 2007, vol. 79, pp. 4805-4813.
L. Marshall et al., "Association and discrimination of diesel fuels using chemometric procedures", Analytical and Bioanalytical Chemistry 2009, vol. 394, No. 8, pp. 2049-2059.
D. Ballabio et al., "Classification of GC-MS Measurements of wines by combining data dimension reduction and variable selection techniques", J. of Chemometrics, 2008, vol. 22, pp. 457-463.
K. Johnson et al., "Pattern Recognition of Jet Fuels: Comprehensive GC x GC with ANOVA-Based Feature Selection and Principal Component Analysis", J. Chemom. Intell. Lab. Syst., 2002, vol. 60, pp. 225-237.
R. Brereton, Applied Chemometrics for Scientists, Chapter 5, John Wiley & Sons, Inc., Toronto, 2007.
B. Weldegergis and A. Crouch, "Analysis of Volatiles in Pinotage Wines by Stir Bar Sorptive Extraction and Chemometric Profiling", J. of Agric. Food Chem., 2008, pp. 10225-10236.
R. Gaines et al., "Chemometric Determination of Target Compounds Used to Fingerprint Unweathered Diesel Fuels", Environmental Forensics, 2006, vol. 7, No. 1, pp. 77-87.
J. Christensen and G. Tomasi, "Practical aspects of chemometrics for oil spill fingerprinting", J. of Chromatography A 2007, vol. 1169, pp. 1-22.
M. Krebs et al., "Alignment of gas chromatography-mass spectrometry data by landmark selection from complex-chemical mixtures", Chemom. Intell. Lab. Syst., 2006, vol. 81, issue 1, pp. 74-81.
T. Rajalahti et al., "Discriminating Variable Test and Selectivity Ratio Plot: Quantitative Tools for Interpretation and Variable (Biomarker) Selection in Complex Spectral or Chromatographic Profiles", Analytical Chemistry, 2009, vol. 81 (7), pp. 2581-2590.
N. Watson et al., "Classification of high-speed gas chromatography-mass spectrometry data by principal component analysis coupled with piecewise alignment and feature selection", J. of Chromatography A, 2006, vol. 1129, pp. 111-118.
K. Pierce et al., "Classification of gasoline data obtained by gas chromatography using a piecewise alignment algorithm combined with feature selection and principal component analysis", J. of Chromatography A, 2005, vol. 1096, pp. 101-110.
R. Teofilo et al., "Sorting variables by using informative vectors as a strategy for feature selection in multivariate regression", J. of Chemometrics, 2009, vol. 23, pp. 32-48.
J. Christensen et al., "Multivariate statistical methods for evaluating biodegradation of mineral oil", J. of Chromatography A, 2005, vol. 1090, pp. 133-145.
S. Wold, "Principal Component Analysis", Chemom. Intell. Lab. Syst., 1987, vol. 2, pp. 37-52.
K. Pierce et al., "Recent advancements in comprehensive two-dimensional separations with chemometrics", J. of Chromatography A, 2008, vol. 1184, pp. 341-352.
R. De Maesschalck et al., "The Mahalanobis distance", Chemom. Intell. Lab. Syst., 2000, vol. 50, pp. 1-18.
K. Pierce et al., "Fisher ratio method applied to third-order separation data to identify significant chemical components of metabolite extracts", Analytical Chemistry, 2006, vol. 78, No. 14, pp. 5068-5075.
R. Brereton, Applied Chemometrics for Scientists, Chapter 7, John Wiley & Sons, Inc., Toronto, 2007.

* cited by examiner

AUTOMATED, OBJECTIVE AND OPTIMIZED FEATURE SELECTION IN CHEMOMETRIC MODELING (CLUSTER RESOLUTION)

TECHNICAL FIELD

The present invention relates to data processing and chemistry. More particularly, the present invention relates to methods and systems for automatically determining which variables to include in a chemometric model.

BACKGROUND OF THE INVENTION

There are many well-established chemometric techniques used to facilitate the handling of chemical data: techniques such as principal components analysis (PCA), parallel factor analysis (PARAFAC), and partial least-squares (PLS) being among the most common. This proliferation of chemometric techniques can be attributed to several factors, including improvements in computing technology and more user-friendly software coupled with advancements in analytical instrumentation. Modern instrumental techniques can provide an abundance of detailed data pertaining to the nature of a complex sample in a relatively short period of time. This in turn has permitted the analyst to probe increasingly complex samples, and pose increasingly challenging questions, the answers of which can only be revealed though the use of chemometric tools.

Some of the most impressively data-rich analytical techniques to which chemometric techniques have been applied include the family of hyphenated separations techniques such as GC-MS and LC-MS as well as comprehensive multidimensional separation techniques such as GC×GC. For example, grades of gasoline were classified based on their GC-MS profiles by Doble et al using PCA. Sandercock and Du Pasquer have used GC-MS coupled with PCA to fingerprint a series of gasoline samples and identify the origin of the samples. Another field where chemometric techniques are widely applied is in metabolomics (as well as general metabolite profiling and metabonomics). Wilson et al. have recently reviewed the application of LC-MS to this field, highlighting some uses of chemometrics. Other examples of the use of chemometrics in this area include Bruce and co-workers who recently evaluated metabolite profiling techniques and used PCA and orthogonal projections to latent structures discriminant analysis (OPLS-DA) on HPLC-MS data, and the work of Lutz et al. who used partial least-squares discriminant analysis (PLS-DA) and PCA in LC-MS/MS-based metabolic profiling to predict gender. Kind et al. applied PLS, PCA and ANOVA to data from a suite of chromatographic-mass spectrometric analyses of urinary metabolites for the early detection of kidney cancer. Now that comprehensive multidimensional gas chromatographic (GC×GC) instrumentation has become commercially available, it (in conjunction with chemometric techniques) is also gaining much interest in this area. For example, Vial et al. used PCA to classify tobacco extracts based on their GC×GC profiles, and Mohler et al. have used GC×GC-TOFMS data and chemometric techniques to analyze yeast metabolites.

When applying chemometric techniques to chromatographic or chromatographic-mass spectrometric data, there are several possible approaches to preparing the data for analysis. Many users employ integrated peak tables of data as this provides a matrix that is relatively small and straightforward: analyte abundances vs. sample numbers. Other users choose to use a non-integrated chromatographic signal for the construction of a chemometric model. With this approach, each variable in the data matrix is the signal intensity at a given time. This route has its own challenges, including increased data size and data alignment; however, these can be overcome relatively easily and this approach is in many cases superior to the use of integrated peak tables. The advantage of using the entire raw data set is more evident when one utilizes the entire GC-MS chromatogram, either as a three-way array (scan number×m/z ratio×sample number) or as a two-dimensional array of samples vs. GC-MS chromatograms unfolded along their time axis. Synovec et al. demonstrated the significant advantages can be achieved by using the entire GC-MS chromatogram rather than extracted ion chromatograms or other univariate signals. The reason for this being that the chemometric model can extract underlying patterns in the data that are not evident in univariate signals.

One challenge that remains for all types of chemometric analyses is that of feature selection: choosing which of the variables that have been collected will be included in the chemometric model. In cases where one is utilizing raw chromatographic data or chromatographic-mass spectrometric data, feature selection becomes at the same time more challenging and more important as millions of variables can be easily collected for each sample. A dataset comprising even a relatively small number of samples such as these will put inordinate demands on a computer system. Apart from the technological challenge, the most important reason for careful variable selection is that not all variables will be relevant. This is especially true when the entire chromatogram is considered: only a small portion of the chromatographic space actually contains relevant signal intensities. If irrelevant variables are included, the model must account for irrelevant variations and this will degrade its overall performance. Consequently, careful variable selection is necessary, especially if raw chromatographic signals are being used in the construction of the model.

There are multiple variable selection techniques that are available, all with the goal of simplifying data sets and removing extraneous variables. Selection techniques such as using integrated peak tables, extracted ion chromatograms (EIC), or single ion monitoring (SIM) rely very highly on a priori knowledge and select variables by only permitting a small, user-selected portion of the data to be used. These are not inappropriate approaches, but they are potentially dangerous, especially if the system is not well understood. The reason for this is that, in these cases, there are numerous opportunities for either the inclusion of significant quantities of irrelevant data or the inadvertent exclusion of relevant portions of the data. Within the scope of chromatography-MS data, total ion chromatograms (TICs) may also be used for modeling, but this sacrifices essentially all of the additional mass spectral information and potentially useful variables in the process.

Objective variable ranking techniques are another option for guiding feature or variable selection. These methods use a calculated metric to evaluate the potential value of each variable. When constructing a model, only those variables with scores above a certain threshold will be used. Examples of the use of objective variable ranking applied to chromatographic data include the work of Rajalahti et al where the discriminating variable (DIVA) test was used to rank variables for both PCA and PLS-DA of chromatographic profiles. Another popular metric for variable ranking is Analysis of Variance (ANOVA) which has been used to guide feature selection for PCA of GC-MS and GC×GC chromatograms. Teófilo et al. have also used informative vectors as the ranking metric prior to PLS analysis of spectroscopic data. Apart from the inherent advantage of objectivity, objective ranking strategies allow the user to consider considerably more candidate variables with no a priori information and can be readily incorporated into automated routines.

A final approach to variable selection is the application of a genetic algorithm (GA). GAs strive to find a suitable set of variables by randomly choosing multiple subsets of variables, evaluating each subset, and then "breeding" a new generation of models by randomly mixing the variables that were included in more successful models. The process then repeats through many generations and a suitable subset of variables is allowed to evolve by chance. The main advantage of GAs is that they can proceed without much user intervention. However, much computational time is required and, they typically exhibit severe overfitting of the data and/or converge to non-optimal solutions, especially with data sets that comprise a large number of variables. Strategies to overcome these limitations have recently been presented by Ballabo et al. However, GAs remain comparatively computationally inefficient.

Regardless of the variable selection technique that is applied, the goals are to remove noise and irrelevant variables while preserving variables that are of value. For example, when techniques such as ANOVA and DIVA are used to select variables to be included in a PCA model, variables are ranked based on their relative ability to discriminate between the classes of samples being considered. Variables with a high ranking are likely to improve class separation, and those with a low ranking are deemed to be irrelevant. As more variables are included, it is more likely that information useful for class discrimination will be included in the model, though each additional variable is likely to be less useful than the previous ones. However, with each new variable more noise is added to the model, possibly reducing the model's ability to discriminate between classes. At some point, the addition of new variables will result in an overall loss of model quality.

This highlights the central problem that must be addressed. In cases where one is attempting to construct a chemometric model of a large data set, how does one objectively choose the optimal combination of features to model the data? Further, how can one quantify and thereby objectively compare the separation and clustering of data points belonging to multiple classes in, for example, a PCA model? This can be judged through visual inspection of various diagnostic plots of the model. However, in order to achieve a fully automated and objective process for feature selection, an objective metric is required.

While metrics for the degree of class separation have been used previously, prior metrics do not account simultaneously for the shapes, sizes and relative orientations of clusters of points on, for example, a PCA scores plot. Such an objective metric should consider these three parameters.

SUMMARY OF INVENTION

The present invention provides a novel metric, termed chemometric resolution, which compares the separation of clusters of data points while simultaneously considering the shapes of the clusters and their relative orientations. This metric, in conjunction with an objective variable ranking metric, allows for the fully-automated determination of the optimal number of variables to be included in a chemometric model of a system. Cluster resolution as defined here is based upon considering the confidence limit at which confidence ellipses constructed around clusters of points representing different classes of objects will still be separated. In one implementation, PCA was used to classify samples of gasoline based upon their octane rating. The entire GC-MS chromatogram of each sample comprising over $2 \times 10^6$ variables was considered. These variables were ranked by ANOVA and then a forward selection approach was used to find the optimal number of variables for inclusion in a model. In this implementation, a model having 2761 variables was found to be optimal. This approach can be generally applied to feature selection for a variety of applications and represents a significant step towards the development of fully-automated, objective construction of chemometric models.

In a first aspect, the present invention provides a method for use in determining which variables are to be included in a chemometric model based on a plurality of data samples, the method comprising:
  a) constructing a chemometric model based on a plurality of variables previously selected
  b) projecting and plotting said plurality of data samples on a coordinate system based on said model constructed in step a)
  c) for each cluster of data points in a plot resulting from step b), defining a predetermined shape that covers a plurality of data points in said cluster using a predetermined percentage of said data points
  d) for each pair of shapes defined in step c), determining a metric which indicates if said shapes are overlapping at said predetermined percentage of said data points
  e) determining if said metric determined in step d) meet or exceed a predetermined standard
  f) in the event said metric does not meet or exceed said standard, adjusting said model and repeating steps a)-e) until said metric meets or exceeds said standard.

In a second aspect, the present invention provides computer readable medium having encoded thereon computer readable instructions for executing a method for use in determining which variables are to be included in a chemometric model based on a plurality of data samples, the method comprising:
  a) constructing a chemometric model based on a plurality of variables previously selected
  b) projecting and plotting said plurality of data samples on a coordinate system based on said model constructed in step a)
  c) for each cluster of data points in a plot resulting from step b), defining a predetermined shape that covers a plurality of data points in said cluster using a predetermined percentage of said data points
  d) for each pair of shapes defined in step c), determining a metric which indicates if said shapes are overlapping at said predetermined percentage of said data points
  e) determining if said metric determined in step d) meet or exceed a predetermined standard
  f) in the event said metric does not meet or exceed said standard, adjusting said model and repeating steps a)-e) until said metric meets or exceeds said standard.

BRIEF DESCRIPTION OF THE DRAWINGS

The drawings show features and advantages will become more apparent from a detailed consideration of the invention when taken in conjunction with the drawings in which.

DETAILED DESCRIPTION OF THE INVENTION

Figure 1A:
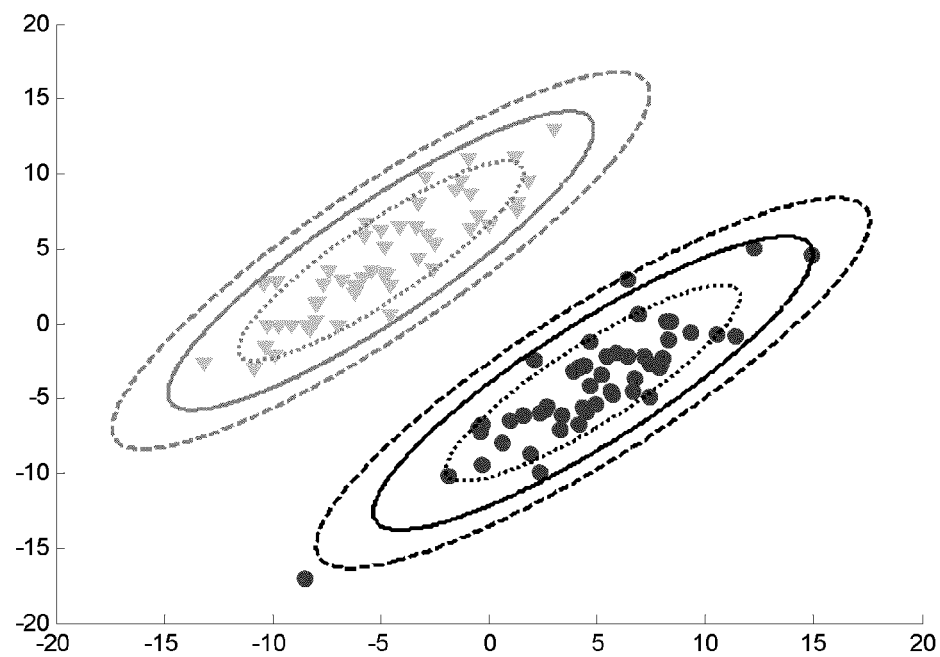
FIG. 1A is a plot of sample ellipses illustrating that relative orientation of the ellipses can have a critical impact on the confidence limit (in this case 75%, 95%, and 99%) at which ellipses can be separated.

As noted above, it is desirable for a metric to consider the shapes, sizes and relative orientations of clusters of points on, for example, a PCA scores plot. Presented below is a metric that compares the separation and orientation of clusters relative to the distance between them. This novel metric has been termed cluster resolution. Also presented below is the use of this metric in a method to automatically construct an optimal PCA model for classifying a series of gasoline samples based upon their GC-MS profiles.

To demonstrate cluster resolution and its use for the automated, optimal feature selection, a test set of gasoline samples was used. Three gasoline samples having octane ratings of 87, 89, and 91 were obtained from a single local gas station in Edmonton, Alberta, Canada. The samples were diluted 20:1 by volume in pentane and analyzed by GC-MS. The GC-MS used for these experiments was a 7890A GC with a 5975 quadrupole MS (Agilent Technologies, Mississauga, ON) equipped with a 30 m×250 µm; 0.25 µm HP-5 column (Agilent). The carrier gas used was helium at constant flow rate of 1.0 mL/min. The injector was held constant at 250° C. and a volume of 0.2 µL was injected with a split ratio of 100:1. The temperature program was 50° C. (3.5 min hold) with a 20° C./min ramp to 300° C. The total run time was 16 min. The initial solvent delay was 2.5 min and mass spectra were collected from m/z 30 to m/z 300 at the rate of 9.2 spectra/s.

A total of 24 chromatograms were collected for each of the gasoline samples over a period of 2 weeks. The entire mass chromatogram for each analysis was exported as a .csv file, which was then imported into MATLAB 7.8.0 (The Mathworks, Natick, Mass.) as a 7400×271 (scan number×m/z ratio) matrix using a lab-written algorithm. Data were then handled in MATLAB using lab-written algorithms. Chemometric models were constructed using PLS toolbox 5.2 (Eigenvector Research Inc., Wenatchee, Wash.).

In discussing the development of the cluster resolution metric, PCA has been used as the example as this is one of the most widely used techniques for data visualization and exploration. Briefly, PCA projects multivariate data with a high dimensionality into a series of orthogonal subspaces, allowing for quick and easy visualization and interpretation of highly dimensional data in a lower-dimensional subspace. The first principal component (PC) explains the most variance within the dataset, and each subsequent component describes less and less variance. For further clarification concerning PCA, reference may be made to Wold and Brereton (see references section below).

While the number of PCs to include in the model is chosen by the user, in practice data are often viewed as plots of scores on combinations of two or three PC axes. When PCA is performed on a dataset containing different classes of samples, each class will ideally cluster in a different region of the scores plot. The size of each cluster will depend on the degree of within-class variation and the distance between each cluster will depend on how well the variability in the included features can describe the differences between the classes. In general it is desirable to have a model where classes are as far apart as possible on the scores plot, while samples within each class are clustered as tightly together as possible. As stated previously, the inclusion of additional relevant variables will drive clusters farther apart, while the addition of less important variables will do little to increase the separation, but will render each cluster of samples more diffuse. In order to automate the variable selection process, a calculable metric must be available that can account for the distance between clusters, while considering their relative orientations and sizes.

It should be noted that metrics for the degree of between-class separation exist in the literature. One straightforward manner in which to measure the separation between classes is to compare the Euclidean distance between the centroids of a pair of classes, relative to square root of the sum of the variance within each group. Another metric compares the sum of Mahalanobis distances between samples belonging to each class and the centroid of the class with the sum of Mahalanobis distances between all samples and the model origin. While these metrics do permit an estimate of between-class separation relative to the sizes of the clusters, they suffer from the fact that they do not consider the shapes and orientations of each class. As demonstrated by FIGS. 1A-1B, the relative orientation of a pair of ellipses can have a critical impact on whether they are separated or not. While all confidence ellipses constructed around the clusters in FIG. 1A are clearly separated, some pairs overlap in FIG. 1B, even though the centroids of these two clusters as well as variance within each class were identical in both cases. In fact, to the metric based on Euclidean distance measurements, these two cases have the same test statistic. To the cluster resolution metric, the cases in FIG. 1A-1B are easily distinguishable, demonstrating a more accurate measure of class separation and a superior metric for automating the process of variable selection.

Figure 1B:
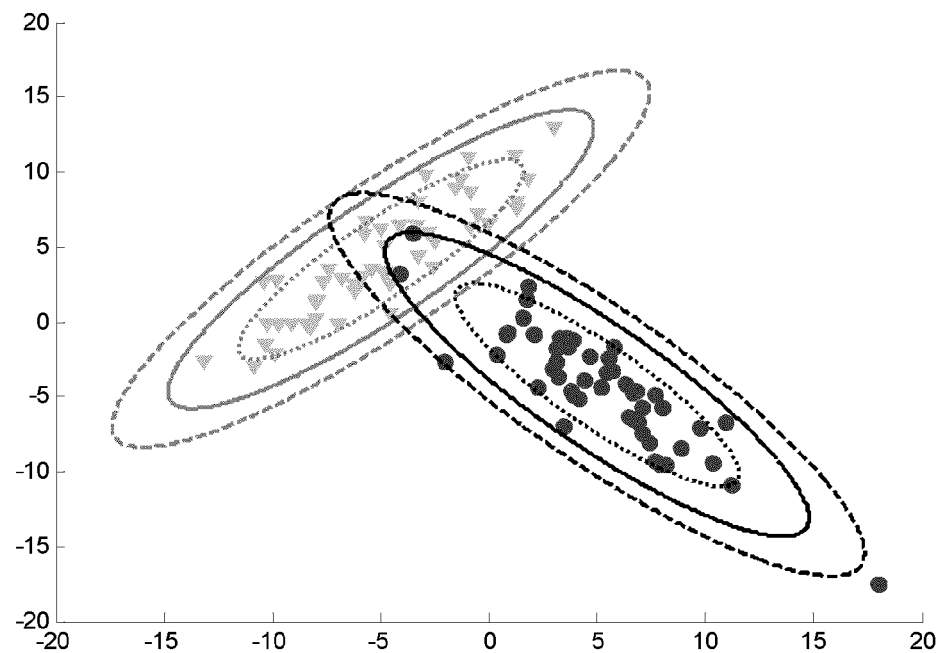
FIG. 1B is a similar plot to FIG. 1A showing ellipses that have the same sizes and origins, but different orientations.

For greater clarity, it should be noted that FIGS. 1A-1B illustrated two clusters of points with 75, 95 and 99% confidence ellipses. In FIG. 1A, ellipses are oriented parallel to each other, and in FIG. 1B, ellipses oriented such that they have some overlap. The centroids of the ellipses and the sizes of the ellipses are the same in both Figures.

A novel calculable metric, termed herein as cluster resolution, takes into account class separation as well as the orientation of the confidence ellipses. Cluster resolution is determined based on the maximum confidence limit at which confidence ellipses can be constructed around clusters of points without overlapping. It should be noted that the determination of cluster resolution is only performed after the raw data gathered has been properly processed and plotted so that the clustering of the data may be determined.

It should be noted that a different but related type of metric (termed chemometric resolution) to cluster resolution is also possible to determine cluster or ellipse relationships and may also be used or considered in automated variable selection. Considering the possibilities for a pair of ellipses that describe a pair of clusters of points, there are four possible cases (see FIGS. 6A, 6B, 6C, and 6D). Ranked from the most desirable case to the least desirable case, the ellipses may be separated (FIG. 6A), mildly overlapped (FIG. 6B), crossing (FIG. 6C), or one ellipse may originate inside of the other ellipse (FIG. 6D). For each case, the chemometric resolution is determined differently. It should be noted that the determination of chemometric resolution is only performed after the raw data gathered has been properly processed and plotted so that the clustering of the data may be determined. Once the data has been processed and plotted, a confidence ellipse (in this implementation) is determined for each data cluster. Chemometric resolution is then determined between each pair of ellipses.

Figure 6A:
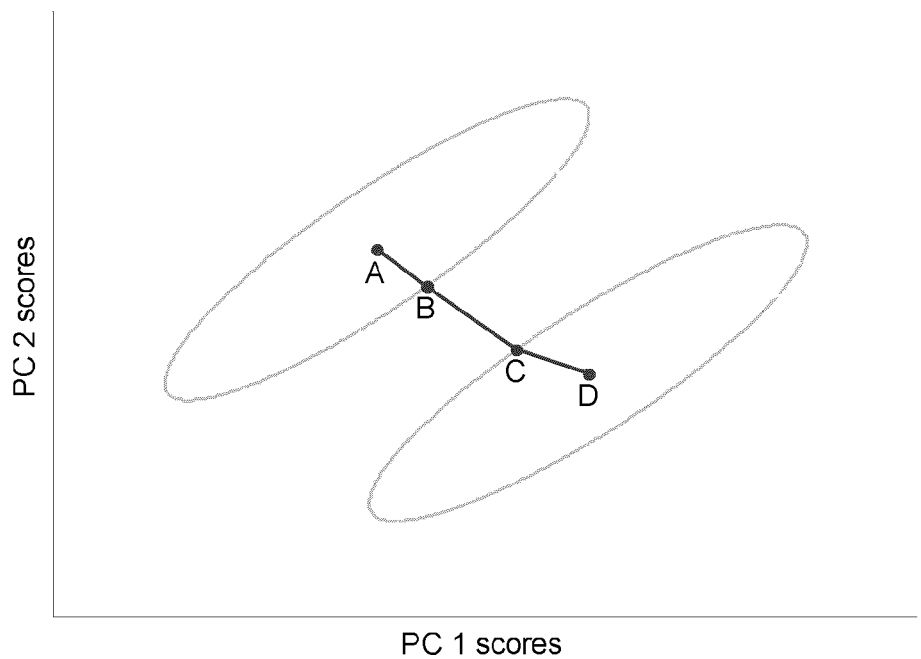
FIG. 6A is a plot of points similar to FIGS. 1A and 1B where the ellipses are separated and used to explain chemometric resolution.
Figure 6B:
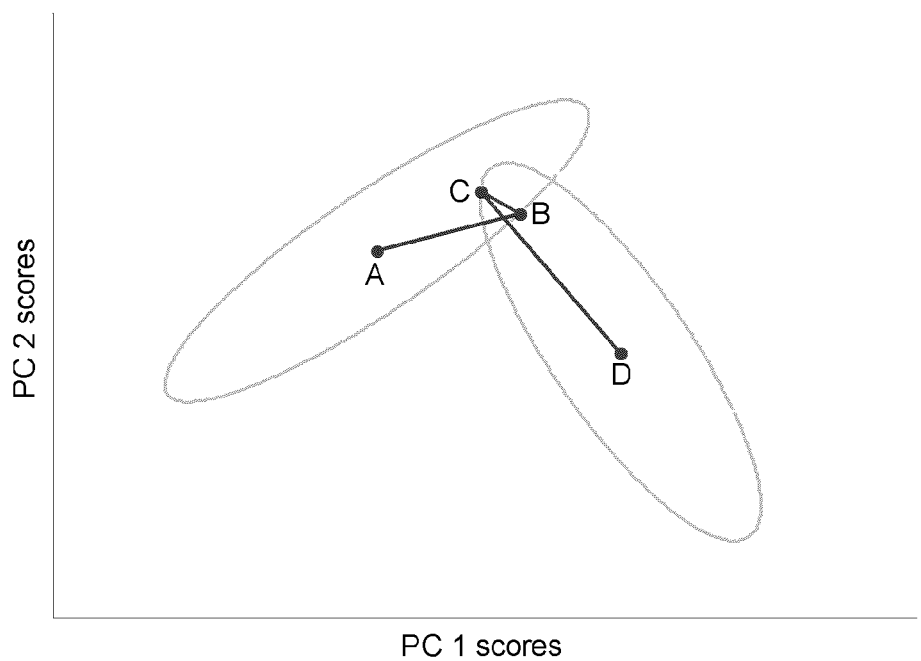
FIG. 6B is a plot similar to FIG. 6A but where the ellipses mildly overlap.
Figure 6C:
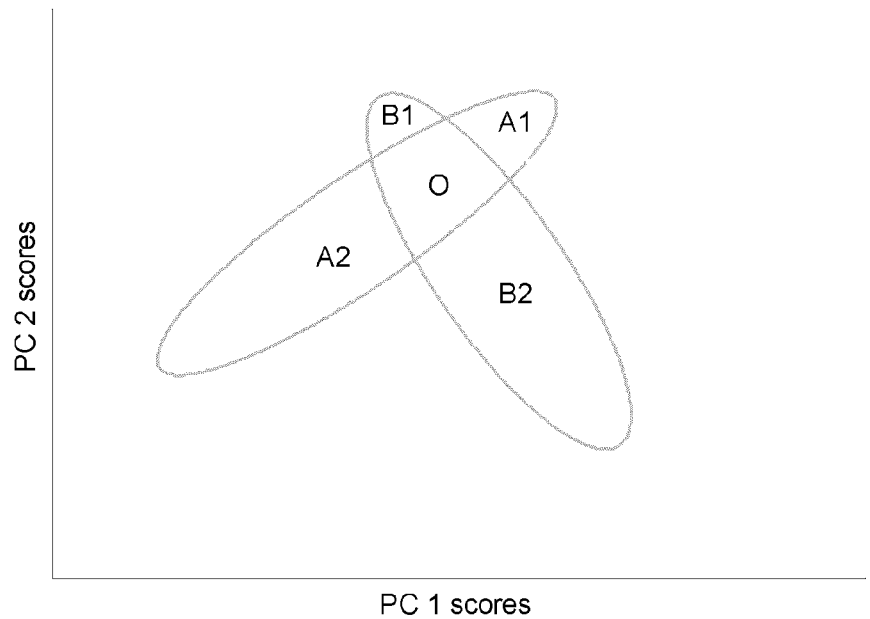
FIG. 6C is a plot similar to FIGS. 6A and 6B but where the ellipses are crossing.
Figure 6D:
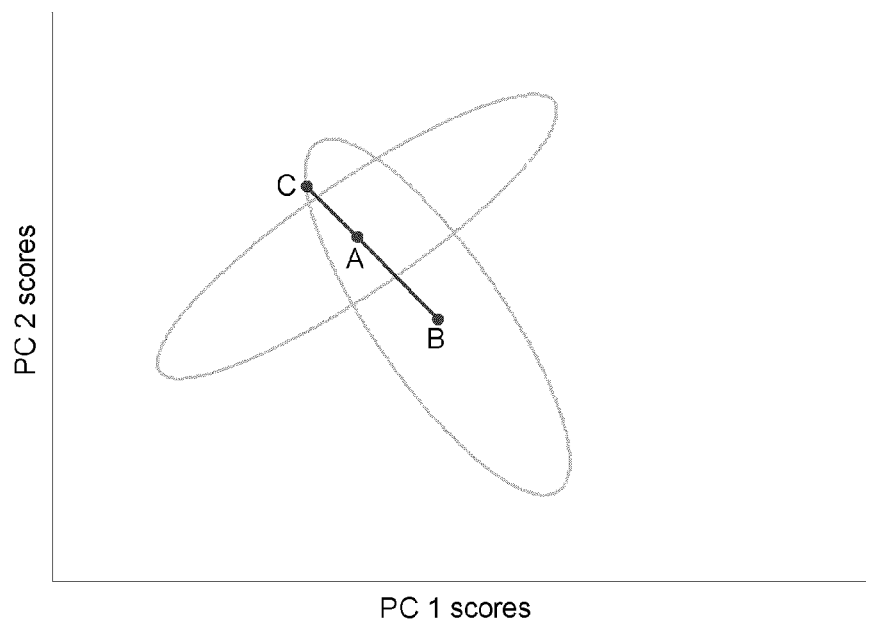
FIG. 6D is a plot similar to FIGS. 6A, 6B, and 6C but where one ellipse originates within another ellipse.

Referring to FIG. 6A, there is depicted the case where the ellipses are separated. Here, chemometric resolution is defined as the distance between the two closest points on the ellipses (line segment BC in FIG. 6A) divided by the average of the distances between the centroid of each ellipse and its point that is closest to the other ellipse (0.5 multiplied by the sum of the distance between points A and B and the distance between points C and D). This is given by Equation 1, where line segments are defined as in FIG. 6A. In this manner, if the ellipses are separated, the resolution will always have a value greater than 0

$$R = \frac{BC}{0.5(AB + CD)} \quad (1)$$

In the case where the ellipses are mildly overlapping (FIG. 6B), a line connecting the two intersections of the ellipses is constructed. At the midpoint of this line, a second, perpendicular line is constructed. The points where this second line intersects the two ellipses are labelled B and C. The resolution is then calculated as in Equation 2. In this case the value is defined to have a negative value, and it will typically have a value between 0 and −1.

$$R = -\frac{BC}{0.5(AB + CD)} \quad (2)$$

In the third case where ellipses are crossing (FIG. 6C) the separation is deemed to be worse than a non-crossing overlap. Resolution is calculated as the ratio of the area contained within the overlap to the total area of the two ellipses (Equation 3). Again, a negative value is assigned. The factor of 1 ensures that the resolution in this case will fall between −1 and −2, and hence can be differentiated from the case of mild overlap.

$$R = -\left(1 + \frac{O}{(O + A1 + A2 + B1 + B2)}\right) \quad (3)$$

The final case is where the centroid of Ellipse 2 lies within Ellipse 1 (FIG. 6D). This is considered the worst possible case. To evaluate the resolution in this case, point C on Ellipse 1 is found at the intersection of Ellipse 1 and a line connecting the centroids of the two ellipses. The distance between point C and the centroid of Ellipse 2 and the distance between the two centroids are then used in Equation 4 to calculate the resolution. The constant −2 is included to ensure that the resolution has a value less than −2 and this case can be differentiated from the other cases.

$$R = -2 - \left(1 - \frac{AB}{AC}\right) \quad (4)$$

The above series of equations provides a metric that allows all possibilities for a pair of ellipses to be considered, ranging from completely separated (resolution>0), to mildly overlapped (0>resolution>−1), to crossing (−1>resolution>−2), to severely overlapping (−2>resolution). However, it should be noted that Equations 3 and 4 are used mostly to determine if the model created is workable or not.

Returning to automated variable selection, the initial step in automated variable selection is to rank the available variables according to some metric, for example ANOVA or DIVA. The choice of ranking metric for the purpose of demonstrating the application of cluster resolution is arbitrary, though it should be noted that it has been observed that different ranking metrics produce different optimal models. A comparison of ranking methods is beyond the scope of the present discussion, but is a topic for future study. Here we have chosen to use ANOVA, which has been described and demonstrated previously, as it is computationally inexpensive and straightforward. Briefly, the output of ANOVA is a series of F ratios for each variable. The F ratio is a measure of the ratio of between-class variance to within-class variance. If a variable has an elevated F ratio, then it is deemed to be more valuable for describing the difference between classes. With the F ratio calculated for every data point in the chromatogram, the variables are ranked in order of decreasing F ratio. A PCA model is then constructed using a fraction of variables that have the highest F ratio. In principle any number of PCs could be used, though for the sake of computational speed, it is best to use as few components as possible. In one implementation, for which the results are presented below, a 2-component model was used.

Once a model is constructed, each class of sample will occupy a given region on the scores plot, and the cluster resolution between each pair of ellipses may then be calculated. This process is repeated, including more and more variables until the desired endpoint is reached. This may be the point where the product of cluster resolutions for all pairs of clusters or the minimum resolution is maximized (i.e. when the critical pair of ellipses is as far apart as possible), or it may be when the product of resolutions or the minimum resolution is greater than a minimum value, for example 0.99. This would be a desirable approach if the end goal is to use the least possible number of variables to obtain an adequate separation between classes.

To determine the ellipse for each group of data points, the cluster that each point belongs to is ideally known beforehand (based on the training set). This information is then used to generate ellipses around the clusters. The separation between the ellipses is then evaluated.

Regarding the specific ellipses, the centroid of each ellipse is found by calculating the average position (x, y) of all the points that make up the ellipse/cluster of points. The equations for the major and minor axes of the ellipse are then found by calculating the two-component PCA model for the single cluster. The vector for PC1 (the first PC) then defines the major axis of the ellipse while the vector for PC2 (the second PC) defines the minor axis. The border of the ellipse is defined by $T^2$ statistic at a given confidence level.

To construct a confidence ellipse for a class, various methods may be used. However, in one implementation, the confidence ellipses were determined by first calculating the covariance matrix of scores:

$$S = \frac{1}{n-1} X'X \quad (5)$$

where S is a scores covariance matrix, n is number of samples in the cluster being evaluated, and X is a matrix where the rows are the samples in a cluster and the columns are the scores of each sample on PCs 1 and 2.

A Singular Value Decomposition (SVD) is then performed on the covariance matrix:

$$ULV' = SVD(S) \quad (6)$$

where U and V' are identical and provide loading vectors for the model describing the confidence ellipse, while L is a diagonal matrix containing eigenvalues for components 1 and 2 of the new model. The number of samples within the cluster permits the determination of the Hotelling $T^2$ value for a given confidence limit:

$$T^2 = \frac{p(n-1)}{n-p} F(\alpha, p, n-p) \quad (7)$$

where p is number of components in a model (in this case 2), n is the number of samples in the class, $\alpha$ is the confidence limit and $F(\alpha,p,n-p)$ is the F statistic for given values of $\alpha$, p and n. The length of each confidence ellipse axis (l) is given by Equation 8.

$$l = \sqrt{T^2 \times L} \quad (8)$$

In this equation, when L is the eigenvalue for PC 1, the length of the major axis is provided, and when L is the eigenvalue of PC 2, the length of the minor axis is provided. With both directions and lengths of the axes describing ellipses at a given confidence limit calculated for each cluster of points, a set of 1000 evenly-spaced points are distributed along the circumference of each ellipse.

To determine if two confidence ellipses overlap at a given confidence level, the Euclidean distances between all points on one ellipse and those on a second ellipse are calculated. The minimum of these distances ($D_{min}$) is compared to half the sum of the distances between two neighbouring points on the circumferences of each ellipse ($D_{critical}$). If the minimum distance, $D_{min}$, is less than the critical distance, $D_{critical}$, the two ellipses are deemed to overlap.

It should be noted that the value for the terms "confidence level" or "confidence limit" vary between 0 and 1 (or 100%) and refer to the term a in Equation 7. It refers to the risk value used in conjunction with n and p degrees of freedom used to determine the value of the f-statistic (or f-distribution) used in Equation 7, where n and p are defined as for Equation 7.

In order to optimize the number of features to be included in the construction of a model, one begins with an arbitrary confidence limit (in one implementation, 75% was chosen) and an initial number of included variables. Any instance of ellipse overlap for this number of variables and arbitrary confidence limit is detected. If overlap is detected, one can iteratively decrease the confidence limit for both ellipses in a stepwise fashion and determine if overlap occurs at each step. This continues until overlap is no longer detected. Conversely, if there is no overlap detected, one can increase the confidence limits of the two ellipses, again in an iterative stepwise fashion, until overlap is detected. The highest confidence limit at which there is no overlap detected is defined as the cluster resolution for a given pair of classes. Cluster resolution is calculated for each pair of classes separately and has values above 0 and below 1 (representing 0 and 100% confidence ellipses).

Cluster resolution is therefore defined as the maximum confidence limit at which confidence ellipses describing two different classes are still separated. In cases where more than two classes exist, cluster resolution is calculated for each pair of ellipses, and then the product of these values or the minimum of these values is used to indicate overall model performance.

During feature selection, variables are added to the model in a forward-selection process. The first time that cluster resolution is determined, the method may begin from an arbitrary confidence limit (e.g. 75%). However, after the first iteration, the cluster resolution for each pair of clusters is stored and used as the starting point for subsequent iterations with additional variables.

Presented here is the proof of concept for this novel metric termed cluster resolution. This metric can be used to automate the feature/variable selection process and compare similar chemometric models in an objective manner. In one implementation, cluster resolution is used to automatically construct a PCA model for different grades of gasoline having the greatest degree of separation between clusters for each class. The first challenge in applying chemometrics to chromatographic data is alignment of the data. In this implementation, chromatograms were aligned using a homemade alignment function based upon the piecewise alignment algorithm developed by Synovec et al. though in principle any alignment algorithm could be used. The aligned matrices were then unfolded along the time axis to yield a series of vectors. ANOVA was then applied to the training set consisting of half of the initial set of 72 chromatograms belonging to three classes using a lab-written method. This yielded a vector of F ratios that was used to rank the features.

With variables now ranked by their F-ratios, the data were autoscaled and subsets of data containing all rows (samples) and the desired number of columns (features) were extracted and used to construct a two-component PCA model. The cluster resolution between each possible pairing of ellipses on the scores plot for PC1 vs. PC2 was then calculated. This step was repeated sequentially, adding more and more variables at each step to find the optimal number of variables to include in the PCA model.

The original data set comprised a matrix with 72 rows (representing samples) and 2005400 columns (representing variables). Half of those data (36 samples) were assigned to the training set and were used for feature ranking, construction of models and calculation of cluster resolution. The other 36 chromatograms were assigned to the test set, which was used for cross-validation of the constructed models. Due to the constraints of addressable memory space in a PC computer with a 32-bit operating system, at most 100000 variables could be considered in a model, though with 64-bit operating systems or smaller data sets this constraint will not exist. Additionally, GC-MS chromatograms are incredibly sparse and this limitation was not an issue in the current study. It took approximately 10 seconds to extract the desired number of features, calculate a PCA model, and evaluate class separation at each step in the optimization process. In order to efficiently determine the optimal number of variables to use, a large step size was used in the first pass through the data to find the approximate location of the optimal number of variables. Then smaller and smaller step sizes were used in the vicinity of the optimum to locate its exact position.

It should be noted that the present invention may also be used with PLS-DA (PLS-Discriminant Analysis), SIMCA (Soft Independent Modeling of Class Analogy), PLS (Partial Least-squares), FA (Factor Analysis), or any other method that generates a scatter plot of data which describes multiple classes.

It should also be clear that ranking methods other than ANOVA may be used. The DIVA (discriminating variable) test may also be used to rank variables for both PCA and PLS-DA of chromatographic profiles. The use of informative vectors as the ranking metric may also be used prior to PLS analysis of spectroscopic data. Any other ranking method may be used with the invention.

While ranking the variables as outlined above is preferred, such a ranking is not strictly necessary. The present invention provides a method which quantitatively compares different models based on the appearance of the clusters of the data points. Such a broad interpretation of the invention need not use a ranking method for the variables but it is preferred.

Figure 2A:
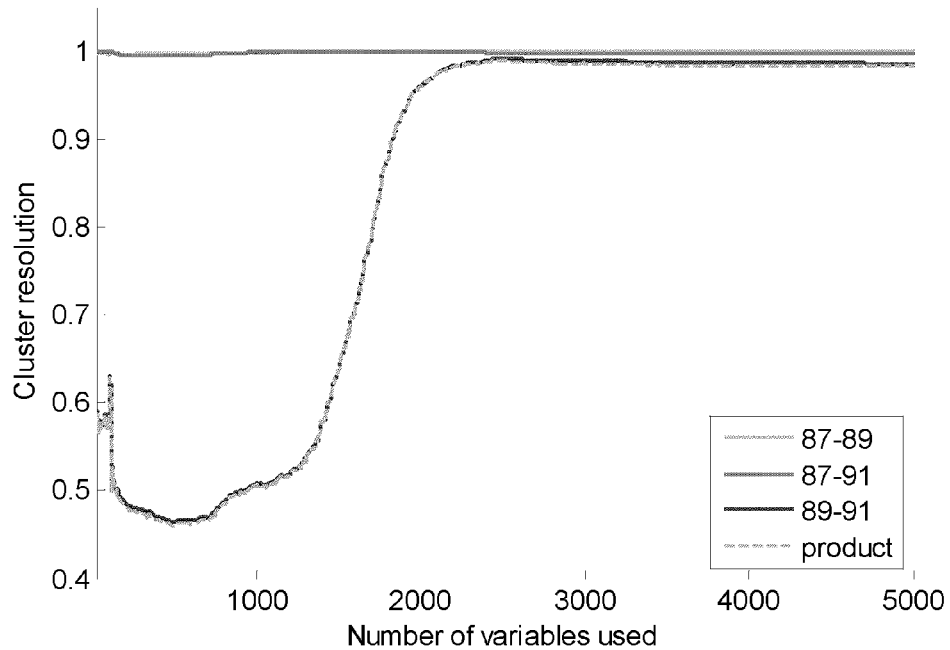
FIGS. 2A-2C illustrate results of an optimization process according to one aspect of the invention.
Figure 2B:
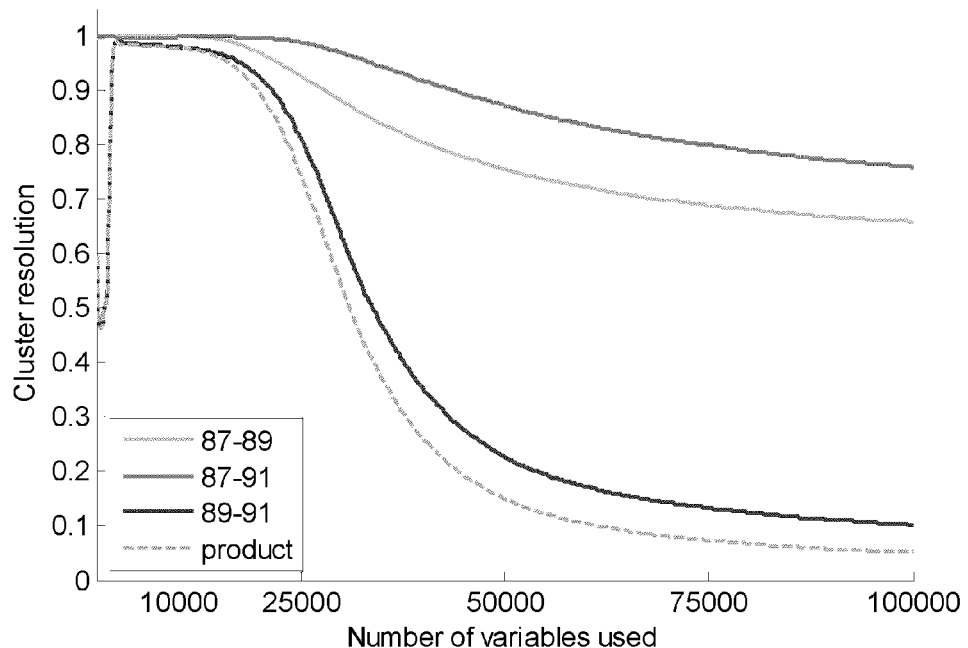
Figure 2C:
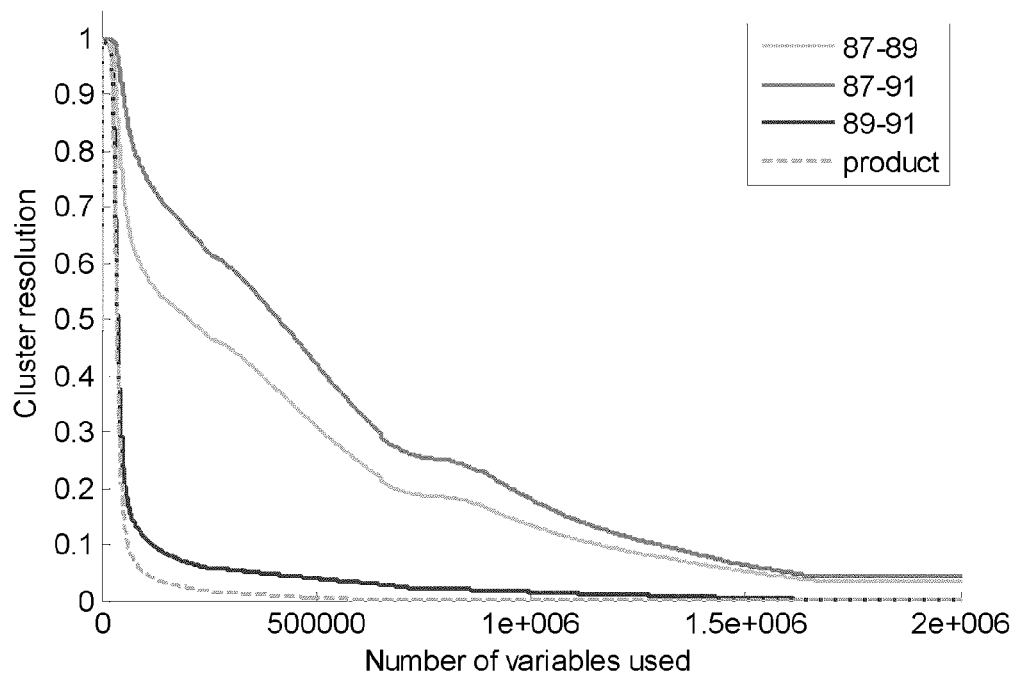
Figure 3A:
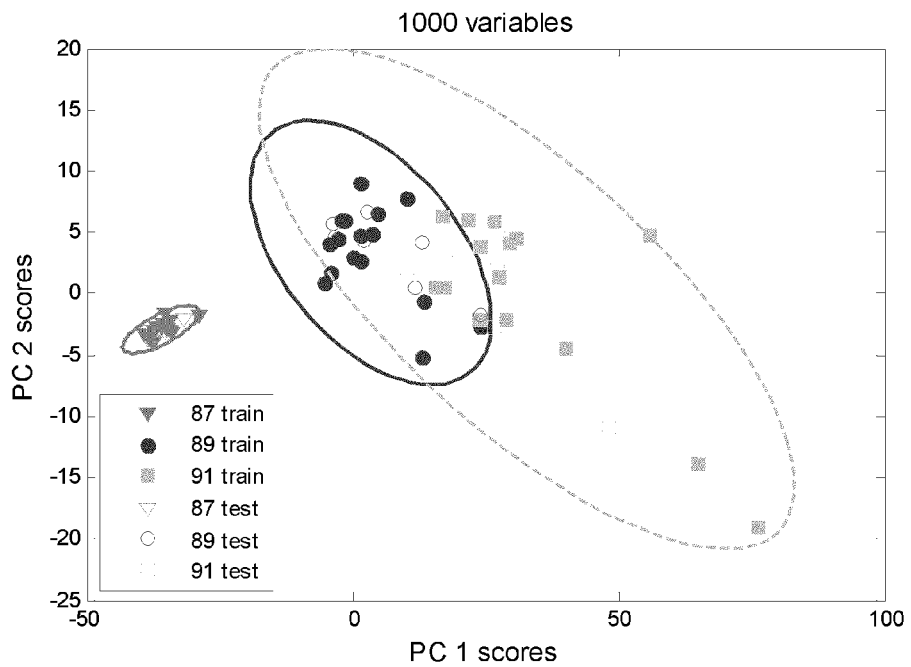
FIGS. 3A-3E are scores plots from 2-component PCA models constructed using different numbers of variables. Filled markers indicate data used to construct the model while hollow markers indicate data used to validate the model.
Figure 3B:
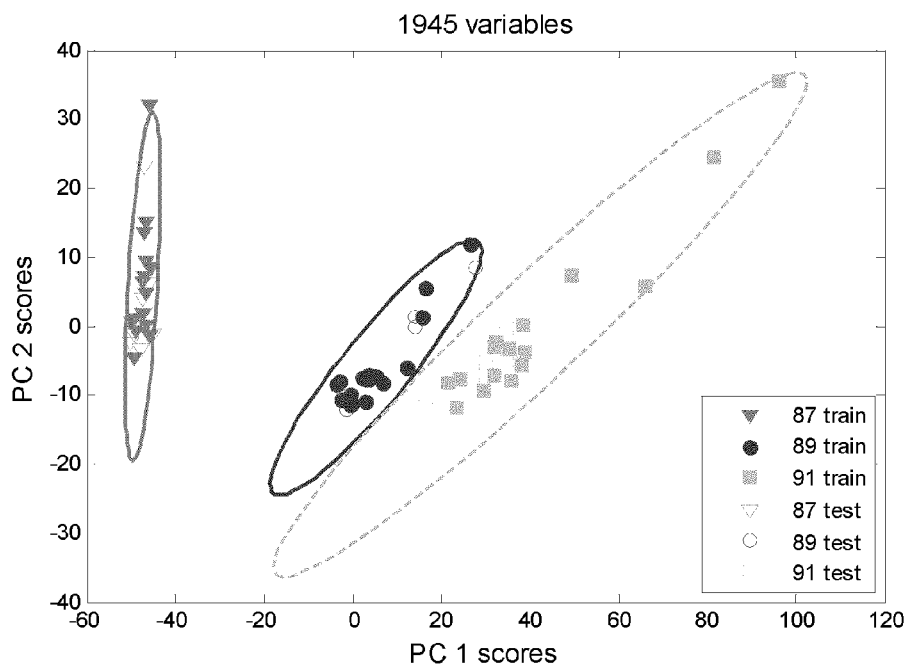
Figure 3C:
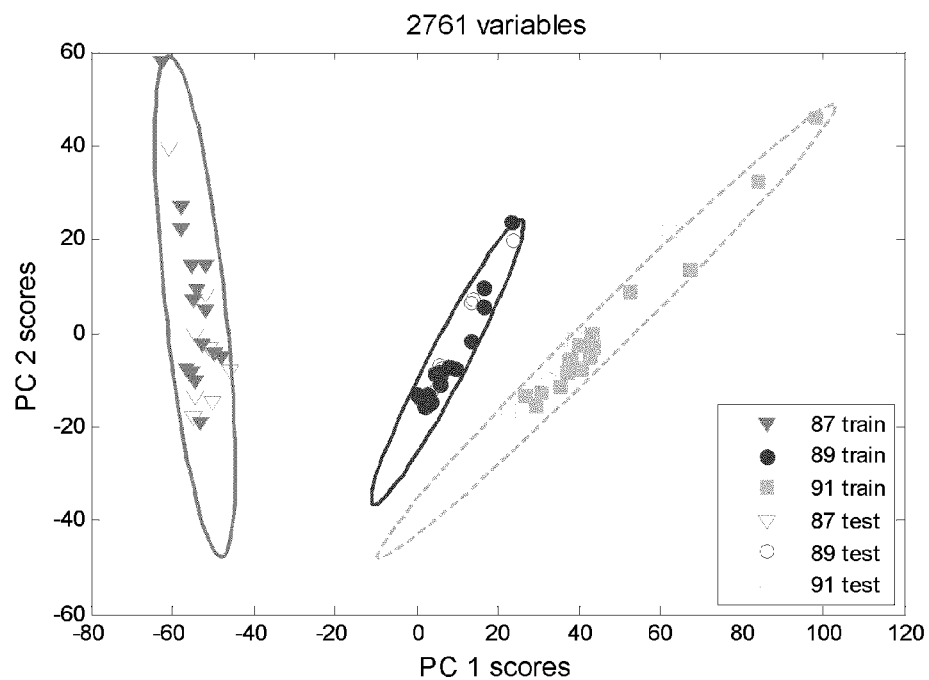
Figure 3D:
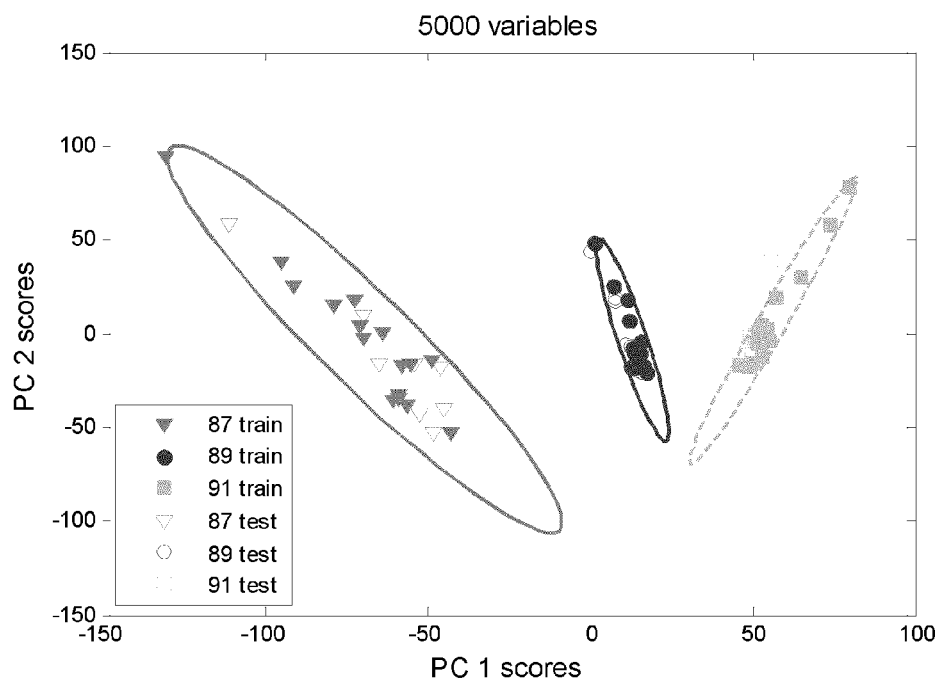
Figure 3E:
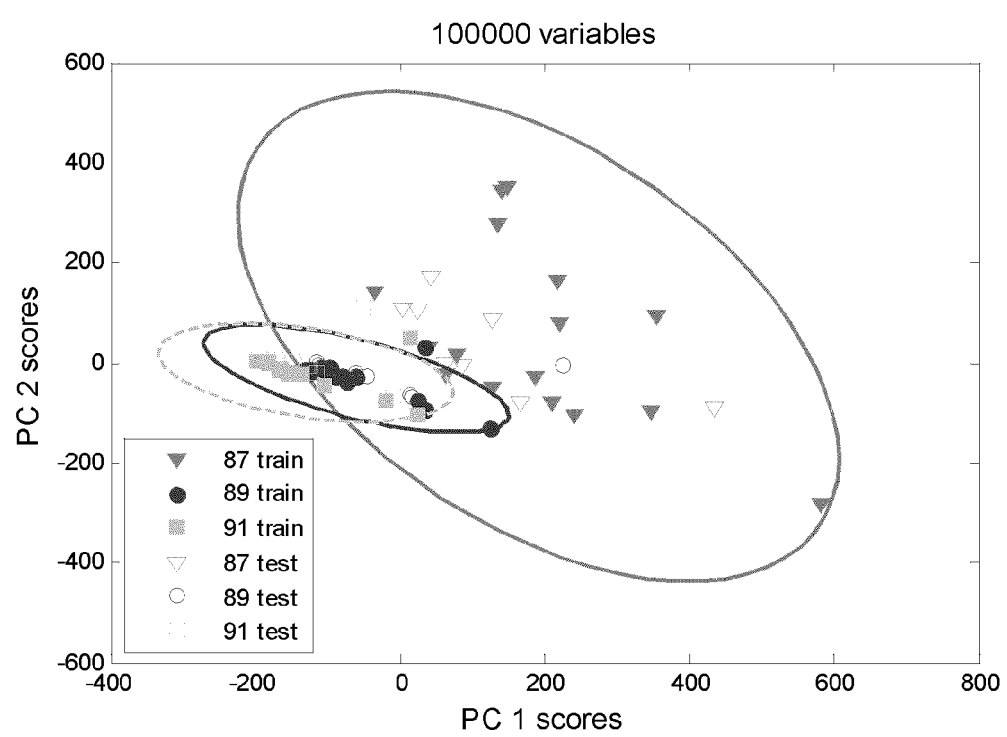

FIG. 2 depicts the results of the optimization process. The Figure depicts the resolution of gasoline clusters as a function of the number of variables used for Set 1. FIG. 2A shows a close up of the region from 0 to 5000 included variables. FIG. 2B shows a close up of the region from 0 to 100 000 included variables. FIG. 2C shows a full resolution plot from 0 to 2 000 000 included variables. In these figures, cluster resolution between pairs of ellipses is plotted on the y-axis vs. the number of features that are included in the model. It is apparent from FIG. 2 that with few variables it is relatively easy to model the differences between 87- and 89-octane gasolines and 87- and 91-octane gasolines. Conversely, it is difficult to distinguish between 89- and 91-octane gasolines, which represent the critical pair of clusters in this case. As the number of variables increases, the separation between 89- and 91-octane gasolines shows a sudden marked improvement, reaching a maximum at 2761 variables. As this pair of clusters was always limiting the quality of the model, the optimal number of features was determined based on the resolution of this pair. Investigating the trend in resolutions past this optimum, a gradual decrease in the resolution for the critical pair is observed.

FIG. 3 shows the scores plots from the 2-component PCA models constructed using different numbers of variables. These Figures show scores plots for selected PCA models. In these figures, dark grey triangles represent 87-octane gasoline, black circles represent 89-octane gasoline and light grey squares represent 91-octane gasoline. Filled markers represent samples used for feature selection and model construction. Hollow markers represent test data to which model was applied. Also, 95% confidence ellipses are indicated for each class. FIGS. 3A, 3B, 3C, 3D, and 3E show plots for 1000, 1945, 2761, 5000, and 100 000 included variables, respectively. As predicted by the plot in FIG. 2A, a 1000-variable model (FIG. 3A) does not include sufficient features/variables to separate all of the classes at 95% confidence limit and should show overlap of the 89- and 91-octane gasoline samples, while the 87-octane gasoline should be well separated from the other two. A 1945-variable model (FIG. 3B) was constructed when cluster resolution between 89 and 91-octane gasoline samples is 0.95 and it shows 95% confidence limit ellipses around those classes barely separated. The model that is constructed using 2761 variables (FIG. 3C) exhibits the best overall resolution between the three classes; adding additional variables (e.g. the 5000-variable model shown in FIG. 3D) decreases the resolution. In the extreme case when far too many variables are included (100000 variables with results shown in FIG. 3E) the quality of the model is highly degraded, with all ellipses exhibiting significant overlap.

Figure 4A:
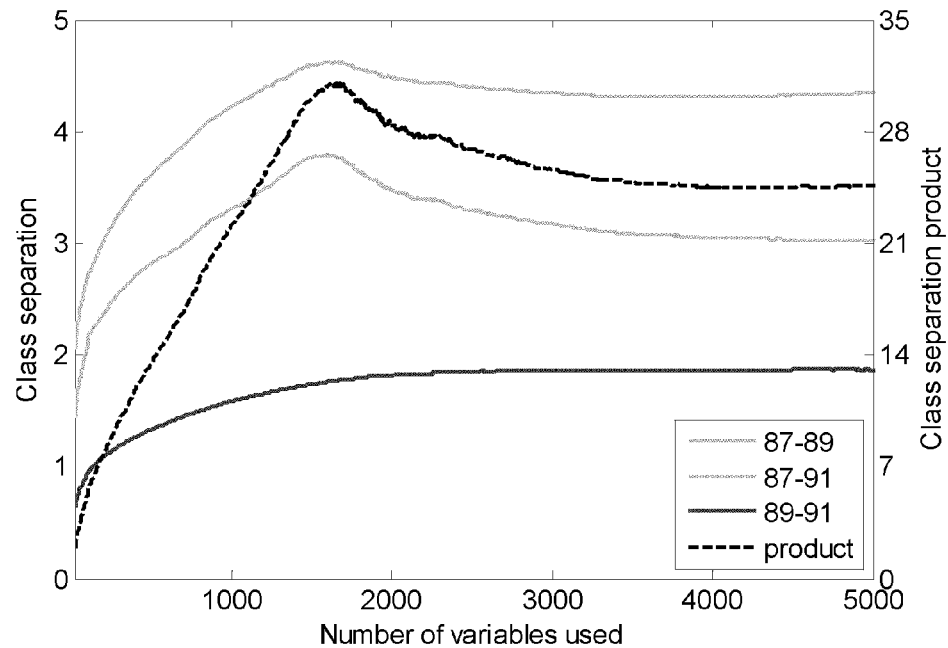
FIGS. 4A and 4B are graphs showing the degree of class separation for each set of classes using identical test data and a different metric.
Figure 4B:
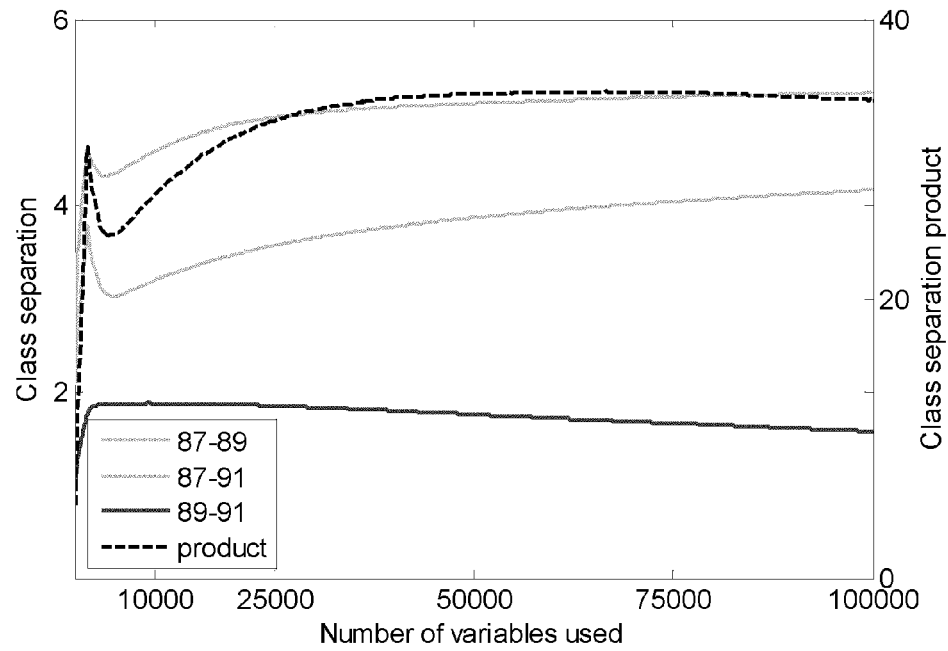
Figure 4C:
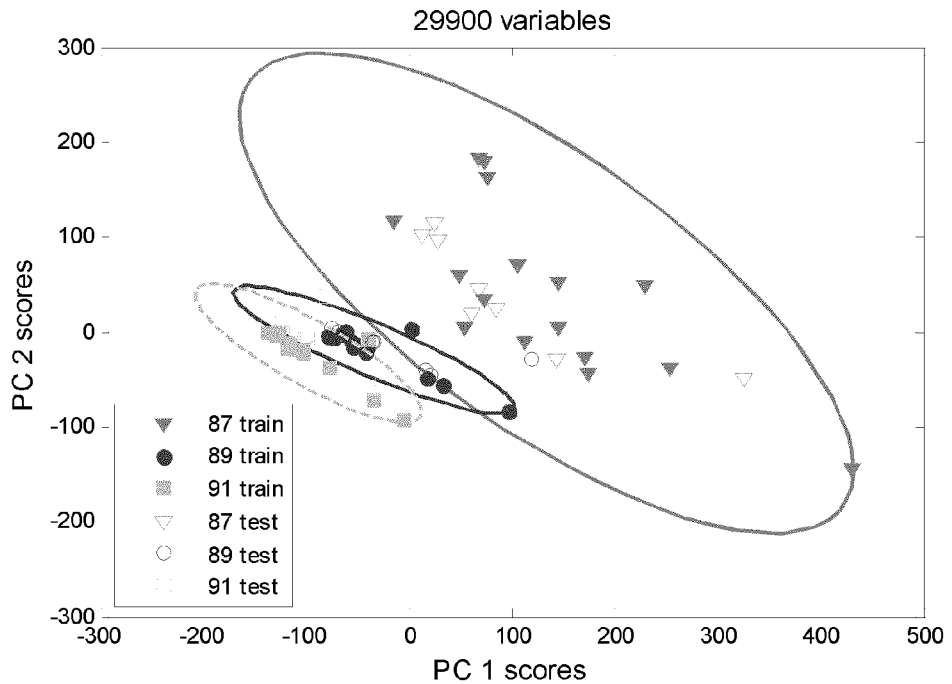
FIG. 4C is a scores plot using the optimum number of variables as illustrated in FIG. 4A.

The cluster resolution metric was compared to a previously described metric based on the Euclidean distance between the centroids of a pair of classes, relative to square root of the sum of the variance within each group. FIGS. 4A-4C illustrate degree of separation vs. number of variables when calculated using a Euclidean distance approach as well as the product of degree of separation for the three classes. FIG. 4A shows a close up of the region from 0 to 5000 included variables. FIG. 4B shows a close up of the region from 0 to 100 000 included variables. FIG. 4C shows a scores plot from PCA model using optimal number of variables found in FIG. 4A. FIGS. 4A and 4B show the degree of class separation achieved for each set of classes using the same test data. When we consider the least separated classes, 89- and 91-octane gasoline, the optimum number of variables predicted by the Euclidean distance metric is 29900, almost an order of magnitude more than the optimum found using the cluster resolution metric.

A visual inspection of the scores plot in FIG. 4C and the one created using the optimum number of variables predicted by the method outlined above using cluster resolution (FIG. 3C) shows that the cluster resolution metric provides a model with a more distinct class separation. The reason for this difference is that the new metric considers simultaneously the shapes, sizes, and relative alignments of clusters.

To better understand the invention, it should be noted that PCA generates a mathematical model to describe the variability in a set of data. The scores on each PC (principal component) are the inner product from the matrix multiplication of the loadings vector for a given principal component with the vector containing all of the variables measured for a given sample. The scores plots can also be viewed as the coordinates of the sample when viewed in the new low-dimensional space defined by the PCA model.

To summarize the method outlined above, a preliminary subset of variables can first be chosen automatically as those variables that contain a total intensity across all samples that are above some threshold. This essentially chooses those variables that contain information, and excludes variables that do not contain any information beyond background noise. In the context of a mass-spectrometric data set, excluded variables would consist of mass channels that had no significantly measureable signal for any of the samples in the training set.

Once variables are ranked, an iterative process begins. First, a chemometric model containing only the presupposed most important variables is constructed. Once this model is constructed, the cluster resolution between all pairs of ellipses is calculated. The process then repeats, including additional variables and the resulting cluster resolutions are recorded. This iterative process continues, providing a series of plots which show the quality of the separation between classes versus the number of variables that are included in the model.

Figure 5:
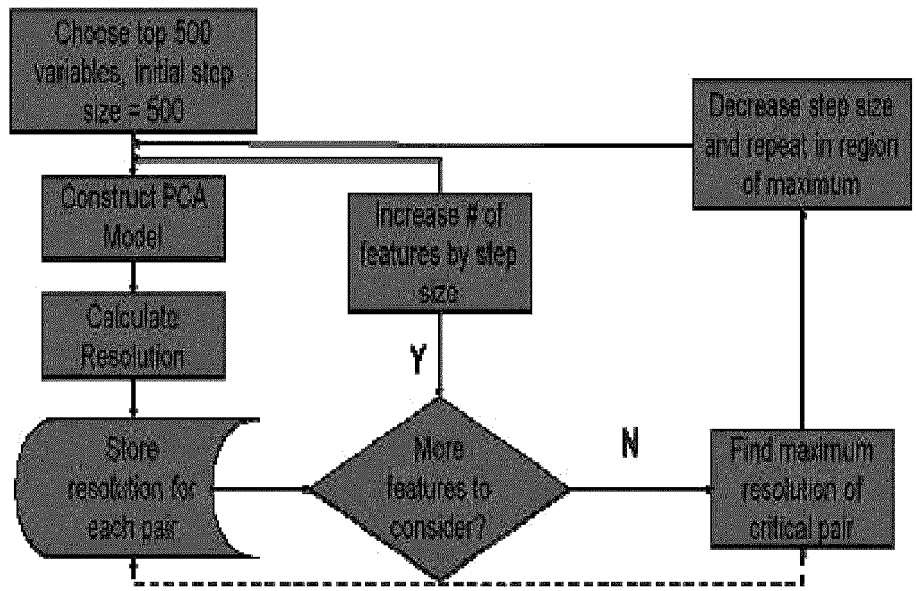
FIG. 5 is a flowchart illustrating the steps in a method for optimizing the number of score plot points used in confidence ellipse definition while maximizing the distance between confidence ellipses.

The optimization process using cluster resolution is summarized in the flowchart of FIG. 5.

Choices of which variables to include can then be made based on these plots. For example, one could include as many variables as required to obtain the best possible resolution, or one could deem that a resolution above a certain threshold (e.g. 0.95) is adequate, and include sufficient variables to obtain this resolution.

In principle, other measures of overlap could be used and the overlap of clusters in higher-dimensional spaces can also be measured in a similar manner. While demonstrated for Principal Components Analysis, this approach could be equally applied to other chemometric techniques.

While the above details a method for determining cluster resolution using 2D plots of data, a 3D version for cluster resolution is also possible. Instead of a 2D (i.e. 2-axis) plot of data, a 3D (i.e. 3-axis) plot of data may be used. 3D ellipsoids may then be used for cluster resolution.

The sizes of ellipsoid axes (i.e. 3 axes in case of a 3-D ellipsoid) are computed in essentially the same way as for a 2-D ellipse. The difference is that points in a cluster are now in 3 dimensions (x, y and z axes). A 3-component PCA model is calculated on that cluster of points (as opposed to a 2-component model for a 2-D ellipse). Confidence limits are calculated for each of 3 components in the same way as it is for each of 2 components in the 2-D ellipse (see above). There is therefore obtained 3 ellipsoid axes (their magnitudes and directions). As well, there is obtained the location of the centroid of the ellipsoid in the same manner as for the 2-D ellipse.

With the magnitudes of ellipsoid axes known, the construction of the unrotated ellipsoid (right size and shape, wrong orientation and position) can proceed. A 3-D ellipsoid will consist of multiple 2-D ellipses parallel to a plane formed by axes 1 and 2 (of the 3-D ellipsoid) with points evenly spaced along the ellipsoid surface.

The first step in constructing the 3D ellipsoid is to calculate the circumference of a 2-D ellipse that lies in the plane of axes 1 and 2 (largest and middle—Principal Components 1 and 2) of the ellipsoid. Basically, it is a slice of the 3-D ellipsoid. Calculation is done in the same manner as for the 2-D ellipse. Next, the circumference is divided by 100 (this number can be changed—a larger number will result in better accuracy (at diminishing returns) with greatly increased computational time). This provides a "minimal distance" between points on the ellipsoid. This value is used to create a 3-D ellipsoid with points evenly distributed along its surface. This is never changed throughout the ellipsoid construction.

Next, an ellipse is created in the plane of axes 1 and 3 (largest and smallest axes—Principal Components 1 and 3). On a 180 degree arc of this ellipse (starting at the tip of axis 3, going through the tip of axis 1 and ending at the other tip of axis 3), points are placed that are spaced at least 1 "minimal distance" apart. Creating evenly spaced points is done in the same manner as in creation of 2-D ellipse. From the locations of each of those points their projections are calculated on the axis-1 and the axis-3 of the ellipsoid as follows:

1: the ratio between projection on axis-1 and value for axis 1 will give a factor by which the axes of the 2-D slices on the ellipsoid (value is never more than 1) will be multiplied 2: the offset by which the slice of the 3-D ellipsoid along the axis 3 will be "raised" or "lowered" (thus, each slice will be parallel to axes 1 and 2). The offsets will not be equal along the z-axis.

With those values calculated, a series of 2-D ellipses are then constructed. The construction is done the same way as before with a notable exception that "minimal distance" value used is always the same as was calculated from the 2-D ellipse lying in the plane of axes 1 and 2—as a result "top" and "bottom" ellipses (which are far smaller) will have few points. Those ellipses are stored in a single matrix that has 3 columns (x, y and z value for each point) and number of rows equal to number of points in the ellipsoid (generally ~3000-varies depending on ratios between axes). This is the unrotated ellipsoid.

Two rotation matrices are then calculated as follows:

The first rotation matrix is a matrix that rotates a vector that lies in the x-axis ([1 0 0]) into the direction of the major axis (Axis 1) of the ellipsoid. Multiplying the unrotated 3-D ellipsoid by this matrix will give a partially rotated 3-D ellipsoid.

The second rotation matrix will rotate the partially rotated 3-D ellipsoid around its axis 1 so that the directions of axes 2 and 3 on the partially rotated 3-D ellipsoid match the directions of the calculated axes 2 and 3. Multiplying the partially rotated 3-D ellipsoid by this matrix will give the fully rotated (right alignment), but uncentered 3-D ellipsoid.

The final step in creating the ellipsoid is the addition of the center of the desired 3-D ellipsoid (a variable with [x y z] values) to each point on the fully rotated 3-D ellipsoid.

This step will give a 3-D ellipsoid of the desired size, shape and alignment in the desired position.

With a 3-D ellipsoid for each class, cluster resolution calculations are essentially the same, with the only difference being that the calculation of the Euclidian distances are in 3 dimensions instead of 2.

The calculation of the confidence ellipsoid, its construction, and metric application can be expanded to as many dimensions as required. However, it must be kept in mind that adding additional dimensions will require far more calculations and will thereby slow down the system. The current method for creating ellipsoids and determining overlap may not be optimal for higher dimensional spaced but it does work for the 3D space.

The cluster resolution metric presented herein provides a means by which the degree of separation between classes of samples can be objectively quantified in a manner that accounts for the sizes, positions, and relative alignments of the clusters. This is a significant advancement and step forward in the development of automated feature selection and automated chemometric model development routines. A manner in which this metric can be incorporated into such a routine for automated optimal feature selection has also been presented. This metric and the general approach to variable selection can in principle be applied to numerous types of chemometric models and with any objective ranking metric for the features. Though demonstrated here as a calculation of two-dimensional ellipses on a two-dimensional plane, it is conceivable that the approach can be extended for use in considering the separation between clusters in higher-dimensional spaces.

The method steps of the invention may be embodied in sets of executable machine code stored in a variety of formats such as object code or source code. Such code is described generically herein as programming code, or a computer program for simplification. Clearly, the executable machine code may be integrated with the code of other programs, implemented as subroutines, by external program calls or by other techniques as known in the art.

The embodiments of the invention may be executed by a computer processor or similar device programmed in the manner of method steps, or may be executed by an electronic system which is provided with means for executing these steps. Similarly, an electronic memory means such computer diskettes, CD-Roms, Random Access Memory (RAM), Read Only Memory (ROM) or similar computer software storage media known in the art, may be programmed to execute such method steps. As well, electronic signals representing these method steps may also be transmitted via a communication network.

Embodiments of the invention may be implemented in any conventional computer programming language For example, preferred embodiments may be implemented in a procedural programming language (e.g."C") or an object oriented language (e.g."C++", "java", or "C#"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server over the network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

References

Doble P.; Sandercock M.; Du Pasquier E.; Petocz P.; Roux C.; Dawson M. Forensic Sci. Int. 2003, 132, 26-39.
Sandercock P. M. L.; Du Pasquier E. Forensic Sci. Int. 2003, 134, 1-10.
Sandercock P. M. L.; Du Pasquier E. Forensic Sci. Int. 2004, 140, 43-59.
Sandercock P. M. L.; Du Pasquier E. Forensic Sci. Int. 2004, 140, 71-77.
Wilson I. D.; Plumb R.; Granger J.; Major H.; Williams R.; Lenz E. M. J. Chromatogr. B 2004, 817, 67-76.
Bruce S. J.; Johnsson P.; Antti H.; Cloarec O.; Trygg J.; Marklund S. L.; Moritz T. Anal. Biochem. 2008, 372, 237-249.
Lutz U.; Lutz R. W.; Lutz W. K. Anal. Chem. 2006, 78, 4564-4571.
Kind T.; Tolstikov V.; Fiehn O.; Weiss R. H. Anal. Biochem. 2007, 363, 185-195.
Vial J.; Nocairi H.; Sassiat P.; Mallipatu S.; Cognon G.; Thiébaut D.; Teillet B.; Rutledge D. N. J. Chromatogr. A 2009, 1216, 2866-2872.
Mohler R. E.; Tu B. P.; Dombeck K. M.; Hoggard J. C.; Young E. T.; Synovec R. E. J. Chromatogr. A 2008, 1186, 401-411
Mohler R. E.; Dombek K. M.; Hoggard J. C.; Pierce K. M.; Young E. T.; Synovec R. E. Analyst 2007, 132, 756-767
Borges C. R. Anal. Chem. 2007, 79, 4805-4813.
Marshall L. J.; McIlroy J. W.; McGuffin V. L.; Waddell Smith R. Anal. Bioanal. Chem. 2009, 394, 2049-2059.
Ballabio D.; Skov T.; Leardi R.; Bro R. J. Chemometrics 2008, 22, 457-463.
Johnson, K. J.; Synovec, R. E. Chemom. Intell. Lab. Syst. 2002, 60, 225-237.
Brereton R. G.; Applied Chemometrics for Scientists. John Wiley & Sons, Inc., Toronto, 2007.
Weldegergis B. T.; Crouch A. M. J. Agric. Food Chem. 2008, 10225-10236.
Gaines R. B.; Hall G. J.; Frysinger G. S.; Gronlund W. R.; Juaire K. L. Environ. Forens. 2006, 7, 77-87.
Christensen J. H.; Tomasi G. J. Chromatogr. A 2007, 1169, 1-22
Krebs M. D.; Tingley R. D.; Zeskind J. E.; Holomboe M. E.; Kang J.; Davis C. E. Chemom. Intell. Lab. Syst. 2006, 81, 74-81.
Rajalahti T.; Arneberg R.; Kroksveen A. C.; Berle M.; Myhr K.-M.; Kvalheim O. M. Anal. Chem. 2009, 81, 2581-2590.
Watson N. E.; VanWingerden M. M.; Pierce K. M.; Wright B. W.; Synovec R. E. J. Chromatogr. A 2006, 1129, 111-118.
Pierce K. M.; Hope J. L.; Johnson K. J.; Wright B. W.; Synovec R. E. J. Chromatogr. A 2005, 1096, 101-110.
Teófilo R. F.; Martins J. P. A.; Ferreira M. M. C. J. Chemometrics 2009, 23, 32-48.
Christensen J. H.; Hansen A. B.; Karlson U.; Mortensen J.; Andersen O. J. Chromatogr. A 2005, 1090, 133-145.
Wold S. Chemom. Intell. Lab. Syst. 1987, 2, 37-52.
Pierce K. M.; Hoggard J. C.; Mohler R. E.; Synovec R. E. J. Chromatogr. A 2008, 1184, 341-352.
De Maesschalck R.; Jouan-Rimbaud D.; Massart D. L. Chemom. Intell. Lab. Syst. 2000, 50, 1-18.
Pierce K. M.; Hoggard J. C.; Hope J. L.; Rainey P. M.; Hoofnagle A. N.; Jack R. M.; Wright B. W.; Synovec R. E. Anal. Chem. 2006, 78, 5068-5075.

Having thus described the invention, what is claimed as new and secured by Letters Patent is:

1. A method for use in determining which variables are to be added to or subtracted from a chemometric model based on a plurality of data samples, the method comprising:
   a) constructing, by a processor, a chemometric model based on a plurality of variables previously selected;
   b) projecting and plotting, by said processor, said plurality of data samples on a coordinate system based on said model constructed in step a);
   c) for each cluster of data points in a plot resulting from step b), defining, by said processor, a confidence ellipse that covers a plurality of data points in said cluster using a predetermined percentage of said data points;
   d) for each pair of ellipses defined in step c), determining, by said processor, if said pair of ellipses are overlapping at said predetermined percentage of said data points;
   e) in the event said pair of ellipses are overlapping, decreasing, by said processor, said percentage of data points used in defining said pair of ellipses;
   f) in the event said pair of ellipses are not overlapping, increasing, by said processor, said percentage of data points used in defining said pair of ellipses;
   g) determining if said pair of ellipses are overlapping;
   h) repeating steps e), f), and g) until said percentage of data points is at a maximum without said pair of ellipses being overlapping; and
   i) recursively adjusting, by said processor, said model by adding or subtracting variables from said model.

2. A method according to claim 1 wherein for steps d) and g), an overlap between said pair of ellipses is determined using a method comprising:
- d1) determining Euclidean distances between all points on one ellipse and all points on the other ellipse;
- d2) determining a minimum of said Euclidean distances;
- d3) comparing said minimum of said Euclidean distances to half a sum of distances between two neighbouring points on a circumferences of each ellipse;
- d4) in the event said minimum of said Euclidean distances is less than said half of said sum of distances, concluding that said ellipses do not overlap.

3. A method according to claim 1 wherein step h) comprises determining a maximum value of α (0<α<1) used for defining each one of said pair of ellipses without causing an overlap between said ellipses, an overlap between said ellipses being determined by:
- d1) determining Euclidean distances between all points on one ellipse and all points on the other ellipse
- d2) determining a minimum of said Euclidean distances
- d3) comparing said minimum of said Euclidean distances to half a sum of distances between two neighbouring points on a circumferences of each ellipse
- d4) in the event said minimum of said Euclidean distances is less than said half of said sum of distances, concluding that said ellipses do not overlap.

4. A method according to claim 3 wherein step h) further comprises maximizing a value of α for a Hotelling value $T^2$ $$T^2 = \frac{p(n-1)}{n-p} F(\alpha, p, n-p)$$

where p is number of components in a model, n is a number of samples in a class, α is a confidence limit and F(α,p,n-p) is an F statistic for given values of α, p and n.

5. A method according to claim 4 wherein lengths of axes (I) of said ellipses defined in step c) are defined by $$l = \sqrt{T^2 \times L}$$

where L is an eigenvalue for a first principal component to determine a major axis length and L is an eigenvalue for a second principal component to determine the minor axis length of an ellipse.

6. Non-transitory computer readable medium having encoded thereon non-transitory computer readable instructions for executing a method for use in determining which variables are to be added to or subtracted from a chemometric model based on a plurality of data samples, the method comprising:
- a) constructing, by a processor, a chemometric model based on a plurality of variables previously selected;
- b) projecting and plotting, by said processor, said plurality of data samples on a coordinate system based on said model constructed in step a);
- c) for each cluster of data points in a plot resulting from step b), defining, by said processor, a confidence ellipse that covers a plurality of data points in said cluster using a predetermined percentage of said data points;
- d) for each pair of ellipses defined in step c), determining, by said processor, if said pair of ellipses are overlapping at said predetermined percentage of said data points;
- e) in the event said pair of ellipses are overlapping, decreasing, by said processor, said percentage of data points used in defining said pair of ellipses;
- f) in the event said pair of ellipses are not overlapping, increasing, by said processor, said percentage of data points used in defining said pair of ellipses;
- g) determining if said pair of ellipses are overlapping; and
- h) repeating steps e), f), and g) until said percentage of data points is at a maximum without said pair of ellipses being overlapping;
- i) recursively adjusting, by said processor, said model by adding or subtracting variables from said model.

7. A method according to claim 1 further including executing the following steps prior to step a):
- a1) ranking said variables according to a predetermined metric;
- a2) selecting a plurality of highly ranked variables from variables ranked in step a) for inclusion in said chemometric model.

8. A method according to claim 7 wherein additional variables added to said chemometric model in step i) are selected from variables ranked in step a1).

9. A method according to claim 1 further comprising determining a cluster resolution for each pair of ellipses and determining a product of these cluster resolutions as a cluster resolution for said model.

10. A method according to claim 1 wherein steps e) and f) comprises increasing or decreasing a confidence level used to define said pair of ellipses in step d).

11. A method according to claim 1 further comprising the step of determining, for each pair of ellipses, a minimum number of variables used to construct the model while maximizing a distance between said pair of ellipses.

12. A method according to claim 1 further comprising the step of determining, for each pair of ellipses, a minimum number of variables used to construct the model said represent while maximizing a distance between said pair of ellipses.

* * * * *